United States Patent
Benecke et al.

(10) Patent No.: US 8,148,501 B2
(45) Date of Patent: Apr. 3, 2012

(54) ABSORBENT PROTEIN MEAL BASE HYDROGELS

(75) Inventors: Herman P. Benecke, Columbus, OH (US); Bhima R. Vijayendran, Carlsbad, CA (US); Kevin B. Spahr, Worthington, OH (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

(21) Appl. No.: 12/918,929

(22) PCT Filed: Feb. 23, 2009

(86) PCT No.: PCT/US2009/034873
§ 371 (c)(1),
(2), (4) Date: Oct. 20, 2010

(87) PCT Pub. No.: WO2009/105753
PCT Pub. Date: Aug. 27, 2009

(65) Prior Publication Data
US 2011/0028314 A1 Feb. 3, 2011

Related U.S. Application Data

(60) Provisional application No. 61/030,783, filed on Feb. 22, 2008.

(51) Int. Cl.
*C08H 1/00* (2006.01)

(52) U.S. Cl. ........ 530/410; 502/400; 502/401; 502/402; 502/403; 502/404; 530/378; 530/370; 530/402; 530/345; 106/645

(58) Field of Classification Search .................... None
See application file for complete search history.

(56) References Cited

U.S. PATENT DOCUMENTS

| | | | |
|---|---|---|---|
| 2,763,625 A | 9/1956 | Illingsworth et al. | |
| 2,831,767 A | 4/1958 | Dann et al. | |
| 4,264,493 A | 4/1981 | Battista | |
| 4,349,470 A | 9/1982 | Battista | |
| 4,416,814 A | 11/1983 | Battista | |
| 4,840,756 A * | 6/1989 | Ebersole et al. | 264/485 |
| 5,847,089 A | 12/1998 | Damodaran et al. | |
| 6,004,583 A * | 12/1999 | Plate et al. | 424/486 |
| 6,149,934 A | 11/2000 | Krzysik et al. | |
| 6,310,105 B1 | 10/2001 | Damodaran | |
| 6,486,213 B1 * | 11/2002 | Chen et al. | 514/772.1 |
| 6,602,950 B1 * | 8/2003 | Dentler et al. | 524/832 |
| 6,660,247 B1 | 12/2003 | Gutowska et al. | |
| 6,821,331 B2 | 11/2004 | Damodaran | |
| RE38,913 E | 12/2005 | Pavlyk | |
| 6,979,464 B2 | 12/2005 | Gutowska | |
| 7,056,957 B2 * | 6/2006 | Omidian et al. | 521/99 |
| 2002/0091165 A1 | 7/2002 | Damodaran | |
| 2004/0048955 A1 | 3/2004 | Wada et al. | |
| 2004/0200386 A1 * | 10/2004 | Damodaran | 106/135.1 |
| 2008/0262102 A1 | 10/2008 | Wang et al. | |

FOREIGN PATENT DOCUMENTS

DE 4207465 9/1993

OTHER PUBLICATIONS

"Graft copolymerization of soybean protein isolate and methacrylic acid", Yang et al. Journal of Applied polymer science, vol. 102, 2006, 4023-4029.*
A website reference "Introduction to polymer chemistry".*
Hwang et al., "Equilibrium Swelling Properties of a Novel Ethylenediaminetetraacetic Dianhydride (EDTAD)-Modified Soy Protein Hydrogel", Journal of Applied Polymer Science, vol. 62, 1996, pp. 1285-1293.
Yang et al., "Graft Copolymerization of Soybean Protein Isolate and Methacrylic Acid", Journal of Applied Polymer Science, vol. 102, 2006, pp. 4023-4029.
Rezai et al., "Polymer-Grafted Cellulose Fibers. I. Enhanced Water Absorbency and Tensile Strength", John Wiley & Sons, Inc., 1997, pp. 1463-1469.
Jain et al., "Grafting of Poly(methyl acrylate) onto Sulfite Pulp Fibers and Its Effect on Water Absorbance", Journal of Applied Polymer Science, vol. 105, 2007, pp. 3195-3203.
Zhang et al., Graft Copolymerization of Artemisia Seed Gum with Acrylic Acid under Microwave and its Water Absorbency, Journal of Macromolecular Science, vol. 44, 2007, pp. 881-885.
De Feng et al., "Study of Initiation Mechanism of the Vinyl Polymerization with the System Persulfate/N,N,N$^1$ ,N'-Tetramehtylethylenediamine", Makromolecular Chem., No. 189, pp. 77-83, 1988.
Pourjavadi et al., "*Synthesis and Super-Swelling Behavior of a Novel Protein-Based Superabsorbent Hydrogel*", Polymer Bulletin, No. 57, pp. 813-824, 2006.

* cited by examiner

*Primary Examiner* — Milton I Cano
*Assistant Examiner* — Wenwen Cai
(74) *Attorney, Agent, or Firm* — Diederiks & Whitelaw, PLC

(57) ABSTRACT

Absorbent hydrogels are formed by reacting a protein meal base, a radical initiator and a polymerizable monomer. Optionally, a cross-linking agent and/or a radical accelerant, such as tetramethylethylenediamine (TMEDA) or sodium bisulfite (NaHSO$_3$), is also added to the mixture. Preferably, the radical initiator is ammonium persulfate (APS) or potassium persulfate (KPS), and the cross-linking agent is preferably trifunctional trimethylolpropane trimethacrylate (TMPTMA) or methylene bis acrylamide (MBA). The polymerizable monomer is preferably acrylic acid, or a combination of acrylic acid and acrylamide. The as-formed hydrogel is washed in order to extract non-reactant components from the gel and then dried. The resultant absorbent and superabsorbent hydrogels have high water uptake ratios, and can be utilized for a variety of applications.

20 Claims, 1 Drawing Sheet

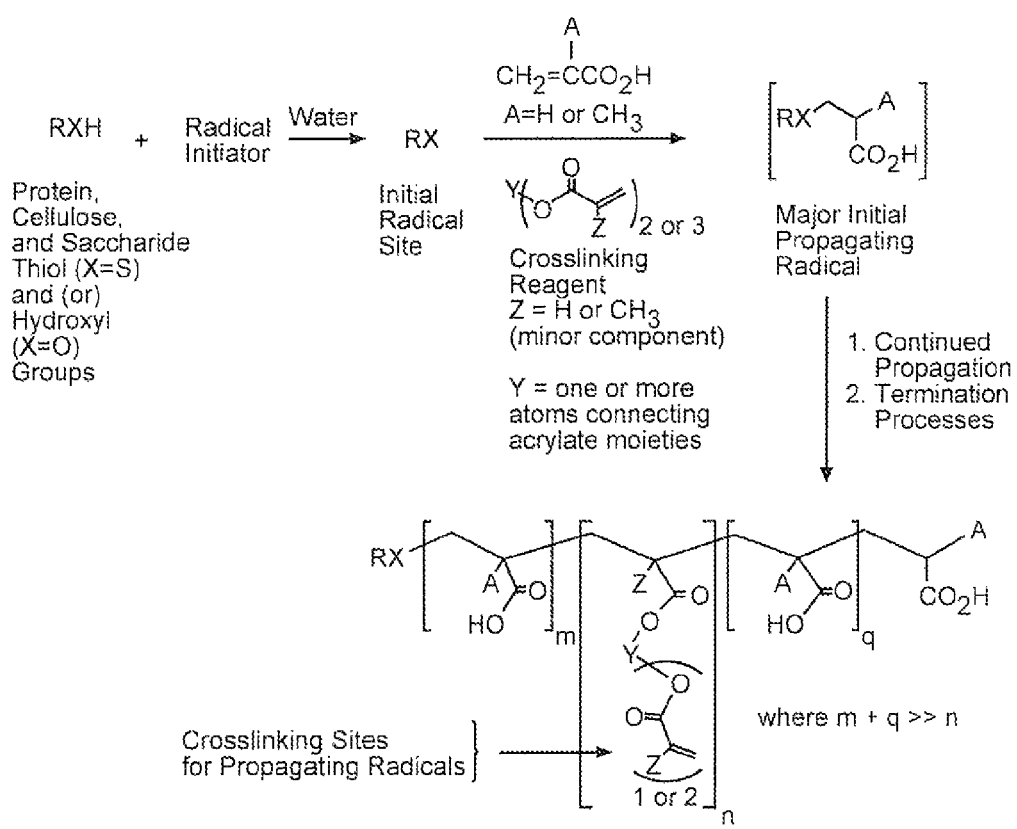

ABSORBENT PROTEIN MEAL BASE HYDROGELS

CROSS-REFERENCE TO RELATED APPLICATIONS

This application represents a National Stage application of PCT/US2009/034873 entitled "Absorbent Protein Meal Base Hydrogels" filed Feb. 23, 2009, pending, which claims priority of U.S. Provisional Patent Application Ser. No. 61/030,783 filed Feb. 22, 2008.

FIELD OF THE INVENTION

The present invention pertains to the field of absorbent and superabsorbent hydrogels and, more specifically, to hydrogels derived from a protein meal base.

BACKGROUND OF THE INVENTION

Absorbent and superabsorbent hydrogels are typically obtained from vegetable or animal proteins, mixtures of vegetable and animal proteins, cellulose, hemicellulose, saccharides (typically C5 and C6 sugars present in plant derived proteins), and polysaccharides. In general, hydrogels are utilized in industrial dewatering applications; maintaining moisture retention in soils, especially in regions experiencing low rainfall; remediation of heavy metal contaminated soil, based on complexation of heavy metal cations with polycarboxylic acids; in control of wildfires, based on application of water-saturated hydrogels; and in diaper and other water/urine absorbing applications.

The combined market for hydrogels is over one billion pounds per year in the U.S. and about 2.5 times that globally, with a growth rate in both markets of approximately 3% per year. Most water-soluble polymers and hydrogels are currently prepared from petroleum-based monomers. Petroleum-based feedstocks for hydrogels include polyvinyl alcohol, polyacrylic acid, polyacrylamide and maleic anhydride/butylene copolymers.

Existing hydrogels are characterized by incorporation of a relatively high percentage of water solubilizing groups such as carboxylic acid, amide and alcohol groups. High performance hydrogels are further characterized by appropriate levels of cross-linking as illustrated in polysuccinimide cross-linked with polyaspartic acid and cross-linked copolymers of maleic anhydride and maleimide.

In prior USDA-funded work, soluble soy protein from soy protein isolate has been converted to high performance hydrogels by using ethylenediaminetetraacetic dianhydride (EDTAD) as the key reagent to provide protein cross-linking and introduce pendant carboxylic acid groups by reaction with lysine amine groups. See D. C. Hwang and S. Damodaran, J. Appl. Polymer Sci. 1996, 62, 1285. See, also U.S. Pat. No. 5,847,089 to Damodaran & Hwang and U.S. Pat. No. 6,310,105 to Damodaran. However, this work has economic disadvantages in that the price of soy protein isolate is fairly expensive and EDTAD is priced at $139/50 g (equivalent to $1262/pound) in the 2007-2008 Aldrich catalog. Currently, EDTAD is not available at bulk scale.

Work by Yang, et al. describes methods for grafting methacrylic acid to the protein in soy protein isolate when using persulfate radical initiators. See C. Yang, et al., Journal of Applied Polymer Science 2006, 102, 4023-4029. However, Yang et al., does not employ acrylate based cross-linkers that are necessary to convert soy protein to a hydrogel. Methods for grafting acrylic monomers to cellulose using ceric ammonium nitrate (Ce(IV)) initiated radical grafting have been described. Although the grafted cellulose products did have somewhat enhanced water absorption compared to non-modified cellulose, none of these products were indicated as having hydrogel properties. See E. Rezai and R. R. Warner, Journal of Applied Polymer Science 1997, 65, 1463-1469; and V. Jain, H. Xiao, and Y. Ni, Journal of Applied Polymer Science 2007, 105, 3195-3203. Hydrogel production using methods for grafting acrylic acid to artemesia seed gum (a natural high molecular weight polysaccharide) using a microwave oven have also been described. See J. Zhang, et al., Journal of Macromolecular Science 2007, 44, 881-885.

SUMMARY OF THE INVENTION

Absorbent hydrogels are formed by grafting a monomer such as acrylic acid or acrylamide with a protein meal base, such as soybean meal. More specifically, a mixture of protein meal base, a radical initiator, a cross-linking agent and a polymerizable monomer is degassed and heated at a temperature of approximately 80° C. for about 2 hours to form an absorbent hydrogel. Optionally, a radical accelerant of tetramethylethylenediamine (TMEDA) or sodium bisulfite ($NaHSO_3$) is also added to the mixture. Preferably, the radical initiator is ammonium persulfate (APS) or potassium persulfate (KPS); and the cross-linking agent is trifunctional trimethylolpropane trimethacrylate (TMPTMA) or methylene bis acrylamide (MBA). The polymerizable monomer is preferably acrylic acid, or a combination of acrylic acid and acrylamide. Useful hydrogel compositions include ratios of acrylic acid to protein meal base between 5:1 and 1:1. Broadly, typical particle sizes for soy meal or bone meal and the like include 100-1500 mesh, preferably between 300-1000 mesh. The as-formed hydrogel is then subjected to a washing process utilizing either water or an organic solvent, an initial water wash followed by washing with organic solvent, or using a mixture of water and organic solvent in order to extract non-reactant components from the gel, before subjecting the gel to a final drying process. The resultant dried absorbent and superabsorbent hydrogels have high water uptake ratios, and can be utilized for a variety of applications.

BRIEF DESCRIPTION OF THE DRAWINGS

FIG. 1 illustrates typical reactions of the invention in grafting and cross-linking of carboxylic functionality to protein, cellulose and saccharide sites.

DETAILED DESCRIPTION OF THE INVENTION

The present invention is generally directed to the formation of absorbent and superabsorbent hydrogels utilizing an animal or vegetable meal base. Useful vegetable proteins sources include, for example, from soy bean meal, cotton seed meal, palm kernel meal or the like. Useful animal proteins include bone meal. At this point it should be noted that the term absorbent hydrogel is meant be inclusive of all hydrogels herein, while the term superabsorbent hydrogel is an absorbent hydrogel (typically a polymer) that can absorb about 100 times or more its weight in water and does not easily release this liquid under pressure.

In accordance with the method of the present invention, monomers are polymerized in the presence of plant or animal meals, or mixtures thereof to produce high performance gels. Monomers that may be utilized include acrylic acid, methacrylic acid, other alpha, beta-unsaturated carboxylic acids or their derivatives, alpha-methyl acrylic acid or acrylamide and its derivatives. It is worth noting that some of the monomers such as acrylic acid noted above could be derived from a renewable bio-source, such as sugars using a fermentation process.

More specifically, the present invention provides for the attachment of alpha, beta-unsaturated carboxylic acids, esters or alpha, beta-unsaturated amides to thiol and hydroxyl groups in protein, cellulose, starch, cellulose, hemicellulose, saccharides and polysaccharides. Useful alpha, beta-unsaturated carboxylic acids or esters include acrylic acid or methyl methacrylate; methacrylic acid or methyl acrylate; maleic acid, maleic anhydride or maleic esters; and itaconic acid and fumaric acid and esters. Useful alpha, beta-unsaturated amides include acrylamide, N-methylacrylamide, and N-ethylacrylamide.

Radical-initiated cross-linking is preferably supplied by the use of polyfunctional acrylate-based cross-linkers such as difunctional polyethylene glycol diacrylate (PEGDA), trifunctional trimethylolpropane trimethacrylate (TMPTMA) and methylene bis acrylamide (MBA). In accordance with the present invention, it was found that the use of tetramethylethylenediamine (TMEDA) in combination with free radical initiators significantly improved hydrogel water uptake values.

In connection with detailing the invention, a schematic of the generalized grafting products from thiol and hydroxyl groups in protein and hydroxyl groups in cellulose and saccharides when starting with acrylic acid is shown in FIG. 1. Cross-linking can occur in the system shown in FIG. 1 by another growing radical that originated from a different RXH site encountering and adding across the cross-linking pendant groups shown. Note that the term m+q>>n signifies that the relative concentrations of cross-linking reagent are much smaller than the concentrations of acrylic or methacrylic acid monomers so that the cross-link density is maintained at appropriately small values to obtain desired high water uptake ratios.

In a preferred method of the present invention, a plant or animal protein meal base is combined with a radical initiator, a cross-linking agent, and a monomer to produce an absorbent hydrogel. Preferably, the radical accelerant TMEDA is also added to the mixture. Optionally, other reducing agents, such as metal sulfites, bisulfites and thiosulfates, may also be utilized. More specifically, a protein meal base, preferably soy meal or bone meal, is admixed with a radical initiator, a cross-linking agent and an aqueous solution of alpha, beta-unsaturated carboxylic acids, acrylamide, N-methylacrylamide or a combination of alpha, beta-unsaturated carboxylic acid, acrylamide and N-methylacrylamide. A meal base to monomer ratio of between 1:1 and 3:1 is preferred. Typically, particle sizes for soy meal, bone meal and the like include 100-1500 mesh, although particle sizes of between 300 mesh and 1000 mesh are preferred for use in the present invention. The resultant mixture is degassed, and the degassed mixture is heated for approximately 2 hours at 80° C. to initiate grafting and polymerization to produce absorbent hydrogel. Optionally, additives may be included in the formation of the hydrogel. For example, clays, such as sepiolite, bentonite and/or hydrotalcite, may be utilized to vary the quantity and rate of water uptake. Additionally, mold inhibitors may be incorporated into the hydrogel compositions.

In a preferred embodiment of the invention, the protein meal base is constituted by soybean meal (or soy meal for short), reduced soy meal, or combinations thereof. Most soy meal is obtained from soybeans by first dehulling the bean and then removing the soybean oil by crushing and optionally extracting the residual oil with a solvent such as hexane. The remaining soy meal is composed primarily of soy protein and some carbohydrate components. The composition of dehulled soy meal is about 12% water, 48% protein, approx. 19-25% cellulose and hemicellulose, 13% sugars, 7% crude fat (if not extracted with hexane) and 3% starch. The following are the weight percentages of the major amino acids in soybean meal: leucine (7.9%), arginine (7.7%), lysine (6.6%), valine (5.3%), isoleucine (5.3%), phenylalanine (5.1%), and cystine (0.7%). Soy meal is mainly water-insoluble in its native form and conventionally requires alkaline and/or chaotropes such as urea or guanidine for dispersal in water. Soy meal may be from about 30% to about 90% protein by weight (typically about 50% to 60% by weight, bone meal is typically 50% to 60% protein by to weight).

Preferred radical intiators include the peroxidic radical initiators ammonium persulfate (APS) and potassium persulfate (KPS). Preferred cross-linking agents include TMPTMA, MBA and PEGDA. Preferred monomers include alpha, beta-unsaturated carboxylic acids such as acrylic acid, acrylamide and combinations thereof, with acrylic acid being the most preferred. Various ratios of acrylic acid to acrylamide may be used to tailor specific water uptake properties. More specifically, acrylic acid has been formed to provide higher water uptake while acrylamide provides increased swollen gel strength. Although a combination of APS and TMEDA is preferred, variable concentrations of other reducing agents in combination with peroxide radical initiators can be utilized to alter water uptake and firmness of the hydrogel.

Once a hydrogel is formed, the as-prepared hydrogel is preferably washed or subjected to an extraction process in order to improve the performance of the gel. This additional process removes unreacted monomers and low molecular weight products, resulting in a final hydrogel product having faster and more efficient water uptake values compared to once-swelled gels.

Advantageously, the above-described methods of the present invention can be utilized to produce a superabsorbent hydrogel. While not intending to limit the present invention, the invention can be readily understood by the examples set forth below.

Experimental Approach

The soy meal utilized in the examples discussed below was Hi-Pro Soybean Meal obtained from Bunge Corporation, White Plains, N.Y. The soy meal was ground and sieved to obtain a particle size less than about 149 microns. All acrylic monomers and cross-linking agents were supplied with phenolic radical inhibitors so all were pre-treated by passing through columns of Aldrich Inhibitor Remover (No. 311332) and then stored at freezer temperatures until use. However, it was found that removal of inhibitor was not necessary if the reactive solution was degassed to remove oxygen which is a strong free radical inhibitor. The oxygen can also be removed at the beginning of the process or at initial steps by bringing the liquids to a boil, or degassing by bubbling an inert gas through the liquid typically with heating. The inert gas can be nitrogen, argon or the like.

Hydrogel Preperation by Grafting Acrylic Acid and Acrylamide to Soy Meal

Initially, it should be noted that, in preparing hydrogel candidates from soy meal, the homopolymers of acrylic acid or acrylamide were not removed and entire polymerized matrices were maintained for hydrogel evaluation. Primarily hydrogel compositions with ratios of acrylic acid to non-modified soy meal ranging from 5:1 to 1:1 on a weight basis were evaluated.

Soy meal was ground and sieved to achieve a particle size of less than 149 microns. Reduced soy meal was optionally prepared by pre-reaction of soy meal with either 2-mercaptoethanol or sodium sulfite to cleave protein disulfide bridges to more reactive thiol groups, and thiol concentrations of reduced soy meal were measured by the colorimetric Ellman method. Water was used as a typical solvent and APS was used as the radical initiator. The percent neutralization of acrylic acid was maintained at 55-80%, preferably about 70%, since percent neutralization of acrylic acid-based hydrogels is known to have a significant effect on properties of hydrogels prepared from carboxylic acid. Ceric ammonium nitrate was also evaluated as a radical initiator since it has been used to graft acrylic esters to cellulose.

Hydrogel preparations were typically performed in a small resin kettle using rapid mechanical stirring. Water used for preparation of sodium hydroxide solutions was initially degassed to help avoid oxygen initiation or termination effects. Before starting grafting reactions, the reaction flask was purged with argon and argon purging was maintained during the reaction. Reactions were initiated by immersing the resin kettle in an oil bath maintained at 80° C.

Since the grafting/polymerization process involved reaction of soy meal slurries in accurately measured quantities of water, the product hydrogels also contained known quantities of water. Water uptake determinations were performed by immersing weighed portions of hydrogels in excess water for 24 hours decanting/blotting off non-bound water. Water uptake ratios were carefully corrected for the percent water present in the hydrogels before testing and were calculated based on their calculated quantity of "dry solids". More specifically, water uptake after immersion in excess water was calculated by the formula:

Weight of swollen hydrogel−calculated dry weight of hydrogel)/(calculated dry weight of hydrogel)

Water uptake results are set forth in Table 1 below.

TABLE 1

Hydrogel Preparation, Gel Properties, and Water Uptake Values

| | Hydrogel Components | | | | | | | | | Hydrogel Properties | | |
|---|---|---|---|---|---|---|---|---|---|---|---|---|
| Prep. No. | Soy Meal (g) | Reduced Soymeal (g) | Acrylic Acid (g) | mL 4.5M NaOH | Acrylamide (g) | Cross-Linker (mg) | APS (mg) | TMEDA (mg) | Ce(IV) (mg) | Polymer Property | Water-Swollen Gel | Water Uptake (g/g) |
| 1 | 2.50 | 0.0 | 5.25 | 11.32 | 0.0 | TMPTMA, 63.1 | 153.5 | 0.0 | 0.0 | good, tack free | good, firm | 180 |
| 2 | 2.51 | 0.0 | 5.25 | 11.32 | 0.0 | TMPTMA, 34.1 | 154.1 | 0.0 | 0.0 | good, tack free | good, firm | 193 |
| 3 | 2.50 | 0.0 | 5.25 | 11.32 | 0.0 | TMPTMA, 17.1 | 153.3 | 0.0 | 0.0 | good, tack free | weak | 209 |
| 4 | 2.51 | 0.0 | 5.25 | 11.32 | 0.0 | MBA, 34.9 | 154.1 | 0.0 | 0.0 | mostly tack free | good, firm | 115 |
| 5 | 2.52 | 0.0 | 5.25 | 11.32 | 0.0 | TMPTMA, 32.8 | 153.4 | 79.2 | 0.0 | good, sl. tacky | good, fairly firm | 241 |
| 6 | 2.51 | 0.0 | 3.68 | 7.60$^d$ | 1.73 | TMPTMA, 34.1 | 154.1 | 0.0 | 0.0 | good, tack free | good, very firm | 148 |
| 7 | 2.51 | 0.0 | 4.73 | 10.20$^d$ | 0.50 | TMPTMA, 29.7 | 153.3 | 0.0 | 0.0 | good, sl. tacky | Good, firm | 183 |
| 8 | 1.675 | 0.827$^a$ | 5.25 | 11.32 | 0.0 | TMPTMA, 33.6 | 154.7 | 0.0 | 0.0 | good, tack free | good, firm | 142 |
| 9 | 1.675 | 0.827$^b$ | 5.25 | 11.32 | 0.0 | TMPTMA, 33.7 | 154.7 | 0.0 | 0.0 | good, tack free | fairly firm | 133 |
| 10 | 1.675 | 0.820$^c$ | 5.25 | 11.32 | 0.0 | TMPTMA, 36.2 | 154.0 | 0.0 | 0.0 | sl. tacky | very poor, weak | 82 |
| 11 | 2.51 | 0.0 | 5.25 | 11.32 | 0.0 | TMPTMA, 34.9 | 0.0 | 0.0 | 100.9 | mushy | very poor, weak | 53 |
| 12 | 1.681 | 0.820 | 5.25 | 11.32 | 0.0 | TMPTMA, 33.7 | 0.0 | 0.0 | 99.6 | tacky, viscous liquid | very poor, weak | 27 |

$^a$Prepared by direct treatment of soy meal with 2-mercaptoethanol;
$^b$Prepared by treatment of soy meal with sodium sulfite followed by extensive washing;
$^c$Prepared by treatment of soy meal with sodium sulfite followed by moderate washing
$^d$3.70 ml degassed deionized water was added to Prep. 6 and 1.13 ml degassed deionized water was added to Prep. 7 to provide same volume water content as other hydrogels in this series.

In general, it is striking that hydrogels described in Table 1 and prepared with an acrylic acid/soy meal ratio slightly greater than 2 gave much better water uptake values than hydrogels prepared from about the same ratio of methacrylic acid to soy protein isolate when methacrylic acid homopolymer was removed by extraction. Visual characterization of these gels indicates that the soy meal in the better performing gels appears to be well dispersed in the gel, without even examining phase behavior by optical or scanning electron microscopy. Meaningful trends in hydrogel properties can be obtained by consideration of data presented in Table 1.

Preparations 1-3 differ only in that the relative concentrations of the trifunctional cross-linker TMPTMA are step-decreased by a factor of two (2) going from Preparations 1 to 3; while the water uptake values vary as follows: Preparation 3>Preparation 2>Preparation 1. However, at the lowest TMPTMA concentration used (Preparation 3), the quality of the water-swollen gel had decreased from firm to weak. Thus, decreasing the concentration of TMPTMA results in a continuing increase in water uptake values but also in a reversal in gel properties at the lowest TMPTMA concentration examined. Comparison of Preparation 2 and Preparation 4 water uptake values indicates that the cross-linker TMPTMA generates a gel with significantly better water uptake (but with equivalent gel properties) than MBA, since about equal weight percentages of these two cross-linkers were used in these two preparations.

Preparations 2 and 5 have almost identical concentrations of TMPTMA and other components, but Preparation 5 used the radical accelerator TMEDA. TMEDA is known to accelerate radical reactions by modifying the reaction pathway to cause TMEDA radicals to be the initiating species (X. De Feng, X. Q. Guo and K. Y. Qiu, Die Makromolekular Chemie 2003, 189, 77-83). It can be seen that the use of TMEDA results in about a 25% increase in water uptake. This effect is considered to be due to an increased radical flux and change in initiation mechanism compared to the normal radical pathway involving APS initiation.

Polyacrylamide was used in Preparations 6 and 7. The composition of Preparation 6 is the same as Preparation 2 except about 33% of the acrylic acid has been replaced with acrylamide. It can be seen that, whereas the to water uptake value of the gel obtained in Preparation 6 was somewhat less than that of Preparation 2, the water-swollen gel was firmer than the gel obtained from Preparation 2. The composition of Preparation 7 is also the same as Preparation 2 except that about 10% of the acrylic acid has been replaced with acrylamide. It can be seen that the resulting water-swollen gel from Preparation 7 is a little less firm than that obtained from Preparation 6, but the water uptake value is also somewhat higher (24%). These combined data indicate that acrylamide provides lower uptake values than acrylic acid in these compositions but does provide firmer water-swollen gels.

Preparations 8-10 have nearly identical compositions as Preparation 2 except that 33% of soy meal was replaced with reduced soy meal that had been reacted with two types of disulfide cleavage reagents. The reduced soy meal used in Preparation 8 was prepared with 2-mercaptoethanol as the disulfide cleavage reagent to produce a product having 44 micromoles thiol group per gram based on the Ellman assay. The reduced soy meals used in Preparations 9 and 10 were both obtained by reaction with sodium sulfite. Sodium sulfite has been reported to cleave protein disulfide bridges so that a thiol is produced on one side and an S-sulfite is produced on the other side of the disulfide linkage. The reduced soy meal used in Preparation 9 was extensively water-washed to remove sulfite, while the reduced soy meal used in Preparation 10 was only moderately water-washed. Ellman assays performed on both samples (even though sulfite will certainly interfere with the Ellman process) indicated very low thiol concentration in reduced soy meal used for Preparation 9 and higher thiol concentration in the soy meal used for Preparation 10 (but presence of sulfite could cause inflated values). It can be seen that these three gels gave lower water uptake values than the gel obtained in Preparation 2 with the following relative water uptake values: Preparation 2>Preparation 8>Preparation 9>Preparation 10. Also, the gels from Preparations 8 and 9 were of fairly high quality but the gel from Preparation 10 was of poor quality. Possibly the thiolated soy meals may have undergone overly effective cross-linking that slowed down water entry into the thiolated protein regions.

Preparations 11 and 12 used ceric ammonium nitrate as the initiator to effectively graft acrylic esters and, less effectively, acrylic acid to cellulose. It can be seen that the gels obtained in these two preparations were of poor quality and had low water uptake values.

Test results for materials prepared using microwave radiation will now be discussed with reference to Table 2 below. Preparations 13 and 14 were subjected to microwave radiation for various time periods as set forth in Table 2. In general, these preparations included soy meal having a particle size of less than 149 microns in a degassed solution of NaOH, acrylic acid, TMPTMA, APS and ceric ammonium nitrate (Ce(IV)). The data in Table 2 indicates that microwave radiation would be useful in preparing hydrogels of the present invention. It can be seen that there are wide variations in water uptake values depending on the irradiation time and number of exposures, and some high water uptake values were observed. This screening work was performed in a Samsung Model MW1150WA standard microwave oven with no control of the microwave wattage.

The example preparations have shown advantages in connection with preparing high capacity hydrogels that contain almost ⅓ soy meal by weight in combination with acrylic acid. A water uptake value of 241 g/g has been obtained in a limited study of the many variables involved in hydrogel performance. It is expected that higher percentages of soy meal may increase water uptake.

TABLE 2

Hydrogel Preparation and Characterization Using Microwave Radiation

| | Hydrogel Components | | | | | | Hydrogel Properties | | |
| --- | --- | --- | --- | --- | --- | --- | --- | --- | --- |
| Prep. No. | Soy Meal (g) | Reduced Soymeal (g) | Acrylic Acid (g) | mL 4.5M NaOH | Cross-Linker (mg) | APS (mg) | Microwave Oven Irradiation Time | Polymer Property | Gel Property | Water Uptake (g/g) |
| 13 | 1.00 | 0.0 | 5.25 | 11.32 | TMPTMA, 10.8 | 133.8 | 1 × 5 sec. | foam structure | weak | ~146 |
| | | | | | | | 2 × 3 sec. | foam structure | weak | ~240 |
| | | | | | | | 3 × 3 sec. | foam structure | weak | ~155 |
| 14 | 2.30 | 0.0 | 5.25 | 11.32 | TMPTMA, 35.2 | 153.1 | 1 × 3 sec. | soft, tacky | weak | 218 |
| | | | | | | | 2 × 3 sec. | soft, tacky | weak | 99 |
| | | | | | | | 3 × 2 sec. | soft, tacky | weak | 139 |
| | | | | | | | 1 × 5 sec. | soft, tacky | weak | 102 |

In addition to the hydrogel formulations discussed above, an additional set of soy meal based hydrogels were produced and evaluated for uptake after extensive washing, as set forth in Table 3 below. The second set of hydrogel preparations were performed in a 50 mL resin kettle including 4.5 M sodium hydroxide in degassed distilled water, for neutralization of acrylic acid to 55%, 70% and 80%, and was stirred for 10 minutes before adding acrylic acid. This mixture was then stirred for 30 minutes at approximately 100 rpm with an argon sparge to remove dissolved oxygen. The catalyst APS or KPS and optionally catalyst reductant TMEDA or sodium bisulfite was added to the mixture and heated for 2 hours at 80° C. Additionally, preparations 6 and 7 were subjected to ultrasound during polymerization in order to obtain a more homogenized gel. It should be noted that modified experimental conditions for preparations 16 and 17 also resulted in hydrogels having desirable properties. More specifically, preparations 16 and 17 were heated for approximately 20 hours at 30° C., rather than 2 hours at 80° C., in the absence of a cross-linking agent or radical accelerant. Hydrogels were then subjected to a washing process, as will be discussed in more detail below.

dry gel weight was compared to the theoretical gel solids weight of the six times swelled gel (aliquot weight/six times swelled gel weight=theoretical solids of the swelled gel) to verify the amount of low molecular weight species removed during water washing.

Water was then added to the vacuum dried water washed gel to confirm the actual or final water uptake for a gel sample of known starting weight and to more accurately measure the water swelling rate. After approximately 24 hours of swell-

TABLE 3

Properties of Hydrogels Prepared from Soy Meal and Acrylic Acid

| | | | | Catalyst Package | | | Water | | Washed Gel after Drying |
| --- | --- | --- | --- | --- | --- | --- | --- | --- | --- |
| Prep. No. | Soy Meal (g) | Acrylic Acid (g) | Cross-Linker: TMPTMA:T or MBA (mg) | Catalyst APS or KPS (mg) | Reductant TMEDA (T) or NaHSO$_3$ (N) | Water-Swollen Gel | Uptake after 6 Rinses(g/g) | Percent Material Extracted | Final Water Uptake (g/g) [aliquot size] |
| 1 | 2.50 | 5.25 @ 70% | T (31.7) | APS (152) | None | firm | 280 | Not determined | 440 [816 mg] |
| 2 | 2.50 | 5.25 @ 70% | T (35) | APS (149) | (T) 0.60 ml | weak | 460 | Not determined | 610 [5.4 mg] |
| 3 | 0.00 | 5.25 @ 70% | T (28.8) | APS (148) | None | firm | 390 | Not determined | 740 [4.4 mg] |
| 4 | 2.50 | 5.25 @ 70% | MBA (19.9) | APS (150) | None | very firm | 220 | 14.9 | 260 [43.8 mg] |
| 5 | 2.51 | 5.25 @ 70% | MBA (19.5) | KPS (138) | (N) 137 mg | firm | 320 | 22.1 | Not determined |
| 6[a] | 0.50 | 1.05 @ 70% | T (6.7) | APS (31.9) | None | Not determined | 354 | Not determined | 1030 [3.4 mg] |
| 7[b] | 0.50 | 1.05 @ 70% | T (6.9) | APS (30.1) | T (36.5 mg) | Not determined | 354 | Not determined | 1060 [3.4 mg] |
| 8 | 2.51 | 5.25 @ 70% | T (26.2) | APS (151) 20 hr at 50 C. | None | Not determined | 512 | 21.7 | Not determined |
| 9 | 2.51 | 5.25 @ 55% | MBA, 4.5 | KPS (136) 3 hr at amb. T. | (N) 136 mg | firm | 650 | 33.4 | 950 [5.9 mg] |
| 10 | 2.51 | 5.25 @ 55% | MBA, 4.5 | KPS (136) 20 hr at amb. T. | (N) 136 mg | firm | 690 | 35.4 | 1380 [4.0 mg] 890 [31.5 mg] |
| 11 | 2.51 | 5.25 @ 55% | T (31.8) | APS (151) | None | firm | 480 | 34.7 | Not determined |
| 12 | 2.50 | 5.25 @ 80% | T (29.6) | APS (150) | None | firm | 830 | 40.1 | 1190 [4.6 mg] |
| 13 | 2.51 | 5.25 @ 80% | T (26.8) | KPS (136) 3 hr at amb. T. | (N) 136 mg | firm | 690 | 32.6 | Not determined |
| 14 | 2.51 | 5.25 @ 880 | T (26.8) | KPS (136) 20 hr at amb. T. | (N) 136 mg | firm | 470 | 34.6 | 1030 [9.2 mg] |
| 15 | 0.00 | 5.25 @ 80% | T (25.7) | APS (152) | None | firm | 1300 | 8.3 | 513 [7.7 mg] 800 [15.5 mg] |
| 16[c] | 2.50 | 5.25 @ 55% | None | APS (104.5) | None | very firm | 578 | Not determined | Not determined |
| 17[d] | 3.00 | 3.0 @ 70% | None | APS (83.1) | None | firm | 305 | Not determined | Not determined |

[a]Modified experimental conditions; ultrasound for 10 mins. followed by reaction at 30° C. for 20 hours.
[b]Modified experimental conditions; ultrasound for 5 mins. followed by reaction at 30° C. for 20 hours (gelled faster during ultrasound)
[c]Modified experimental conditions; heated at 30° C. for 20 hours.
[d]Modified experimental conditions; heated 30° C. for 20 hours, and rinsed 3 times only.

Aliquots of as-prepared hydrogel were placed into an initial volume of distilled water for about 20 hours, resulting in a swelled hydrogel. The swelled hydrogel was separated from any excess water by pouring over a #35 S.S. wire sieve, and the excess water collected and dried. The hydrogel collected on the sieve was patted dry with a paper towel. The weight of the tarred sieve containing the hydrogel was obtained to determine the water uptake ratio (total gel weight—starting gel solids/gel solids) after which the swelled gel was returned to the sample container and additional water was added. This procedure was performing a total of six times with the total water uptake being determined. Values for percent of material extracted were based on the assumption that initially-formed gels contain the same percent water used in their preparation (i.e. 55%).

A small aliquot (4.4-43.8 mg) of the six-times swelled gel was placed into a tarred vial and the gel weight established. The vial with gel was then vacuum-dried at 50° C. for at least 24 hours at which time a dry gel weight was obtained. This ing, during which observations were made to determine swelling rate, the swelled gel was sieved to remove excess water, and a weight of the swelled gel was recorded. The resultant final water uptake value was usually higher than the water uptake value obtained during the initial six-times washed gel because of the removal of unreacted monomers and low molecular weight ingredients, as demonstrated by the results in Table 3. As can be seen from the results, this process produced superabsorbent hydrogels having a water uptake of up to or reaching 1380 g/g.

Although sample results in Table 3 were obtained using the above-identified washing process, certain drawbacks associated with water washing were found to be overcome by utilizing an organic solvent extraction process. In particular, the energy intensive process of drying the six-times swelled hydrogel products can be overcome using a Soxhlet extraction method. As with the washing process, the purpose of the extraction method is to expedite the process of removing unreacted ingredients and low molecular weight species from the as-prepared hydrogel product to achieve improved water uptake values.

A Soxhlet extraction method was performed on as-prepared soy meal gels and gels that were pre-swelled in water with relatively low water uptake ratios of about 75:1 to 150:1. Organic solvents, such as alcohols, ketones and ethers, have been tested for their extraction efficiency, and the best results obtained using methanol. Extraction was found to be most efficiently performed in a Soxhlet extractor as follows: The pre-weighed gel was placed into a glass extraction thimble which was positioned in the Soxhlet extraction apparatus fitted with a water-chilled condenser positioned atop a 250 ml round bottom flask filled with about 150 ml of methanol and heated by an electrical heating mantle. After about 24 hours, the methanol extracted gel was removed and vacuum dried at 50° C. for an additional 24 hours prior to performing water swelling to evaluate the extraction method results. Preferably, the as-prepared hydrogel is pre-swelled in water to 100× to 200×, before Soxhlet extraction in methanol for 24 to 48 hours. This method has proven comparable to the effectiveness of the six-times water washing method.

Although described with reference to preferred embodiments of the invention, it should be readily understood that various changes and/or modifications can be made to the invention without departing from the spirit thereof. For example, relative concentrations of trifunctional cross-linkers such as TMPTMA and difunctional cross-linkers can be altered to impart useful properties. Cross-linking in carboxylic acid grafted protein may be initiated by adding soluble salts incorporating multivalent cations, for example, +2 cations such as calcium and magnesium salts or +3 cations such as aluminum (III) and ferric salts to generate "ionic" cross-linking. Additionally, concentrations of ammonium persulfate may be altered to produce desired hydrogel properties. More specifically, lower concentrations lead to longer grafting claims and higher concentrations lead to shorter grafting chains. Further, different ratios of acrylic acid conjugate acid to conjugate base (salt forms) are useful since different acrylic acid-based hydrogels have optimum hydrogel performance at different conjugate acid/conjugate base ratios. Optionally, the hydrogel formation process may include the Michael addition of protein lysine amino groups to acrylates and polyacrylates and the use of low-cost and high lysine-content bone meal to increase carboxylic acid incorporation and cross-linking. Additionally, in some embodiments, protein meal from palm kernel could be used either alone or in combination with soy meal and bone meal. Therefore, while the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit of the scope of the invention. In general, the invention is only intended to be limited by the scope of the following claims.

What is claimed is:

1. A method for making an absorbent hydrogel comprising:
   a. combining to form a mixture:
      a protein meal base;
      a cross-linking agent;
      a radical initiator; and
      a polymerizable monomer;
   b. degassing the mixture to form a degassed mixture; and
   c. mixing the degassed mixture to initiate grafting and polymerization to produce the absorbent hydrogel.

2. The method of claim 1, wherein the protein meal base constitutes soy bean meal.

3. The method of claim 2, wherein the polymerizable monomer is acrylic acid.

4. The method of claim 3, wherein the ratio of acrylic acid to soy bean meal is between 5:1 and 1:1.

5. The method of claim 1, wherein the protein meal base constitutes soy bean meal, bone meal, palm kernel meal, cotton meal, or combinations thereof.

6. The method of claim 1, wherein the radical initiator is selected from the group consisting of ammonium persulfate and potassium persulfate.

7. The method of claim 1, wherein the degassed mixture is also heated to initiate grafting and polymerization.

8. The method of claim 7, wherein the degassed mixture is heated at a temperature of approximately 80° C. for about 2 hours.

9. The method of claim 1, wherein the cross-linking agent is selected from the group consisting of trifunctional trimethylolpropane trimethacrylate, methylene bis acrylamide, and polyethylene glycol diacrylate.

10. The method of claim 7, further comprising adding sodium hydroxide in an amount to neutralize about 50-80% of carboxylic acid groups present in the mixture.

11. The method of claim 1, further comprising adding a radical accelerant to the mixture.

12. The method of claim 11, wherein the radical accelerant is selected from the group consisting of tetramethylethylenediamine and a metal bisulfate.

13. The method of claim 1, wherein the polymerizable monomer is selected from the group consisting of acrylamide, N-methyl acrylamide, alpha-methyl acrylic acid and combinations thereof.

14. The method of claim 1, further comprising:
   d) washing the absorbent hydrogel in water;
   e) removing excess water from the absorbent hydrogel; and
   f) drying the washed hydrogel to form an absorbent hydrogel having a water uptake greater than a water uptake of the absorbent hydrogel before washing.

15. The method of claim 14, wherein the absorbent hydrogel is a superabsorbent hydrogel.

16. The method of claim 1, further comprising:
   d) washing the absorbent hydrogel with an organic solvent; and
   e) drying the washed hydrogel to form an absorbent hydrogel having a modified water uptake greater than a water uptake of the absorbent hydrogel before washing.

17. The method of claim 16, wherein washing of the absorbent hydrogel is conducted utilizing a Soxhlet extraction apparatus.

18. The method of claim 16, further comprising:
   f) swelling the absorbent hydrogel with water prior to washing the absorbent hydrogel with the organic solvent.

19. The method of claim 16, wherein the absorbent hydrogel is a superabsorbent hydrogel.

20. An absorbent hydrogel produced by the process of claim 1.

* * * * *

UNITED STATES PATENT AND TRADEMARK OFFICE
CERTIFICATE OF CORRECTION

PATENT NO.        : 8,148,501 B2                                              Page 1 of 1
APPLICATION NO.   : 12/918929
DATED             : April 3, 2012
INVENTOR(S)       : Benecke et al.

It is certified that error appears in the above-identified patent and that said Letters Patent is hereby corrected as shown below:

Claim 12, line 3, which is found at column 12, line 32 of the patent, the word "bisulfate" should be changed to --bisulfite--.

Signed and Sealed this
Twenty-ninth Day of May, 2012

David J. Kappos
*Director of the United States Patent and Trademark Office*